US005753270A

United States Patent [19]
Beauchamp et al.

[11] Patent Number: 5,753,270
[45] Date of Patent: May 19, 1998

[54] TOPICAL TREATMENT OF DISEASED SKIN DISORDERS

[75] Inventors: Patrick A. Beauchamp, 1, 1011 Canterbury Drive S.W., Calgary, Alberta, Canada, T2W 2S8; James A. Rogers, 6 Greenridge Drive, Sherwood Park, Edmonton, Alberta, Canada, T8A 5G1

[73] Assignees: Patrick A. Beauchamp; James A. Rogers, both of Edmonton, Canada

[21] Appl. No.: 576,170

[22] Filed: Dec. 21, 1995

Related U.S. Application Data

[63] Continuation of Ser. No. 108,167, Aug. 18, 1993, abandoned, which is a continuation of Ser. No. 715,710, Jun. 18, 1991, abandoned, which is a continuation of Ser. No. 476,141, Feb. 7, 1990, abandoned, which is a continuation of Ser. No. 242,121, Sep. 9, 1988, abandoned.

[30] Foreign Application Priority Data

Sep. 16, 1987 [CA] Canada ........................... 546981

[51] Int. Cl.⁶ .................................................. A61K 33/36
[52] U.S. Cl. ........................ 424/667; 514/556; 514/724; 514/728
[58] Field of Search ..................... 424/667; 514/556, 514/724, 728

[56] References Cited

U.S. PATENT DOCUMENTS

| 54,763 | 1/1866 | Bourdil | 424/150 |
|---|---|---|---|
| 608,612 | 8/1898 | Klever | 424/150 |
| 4,294,852 | 10/1981 | Wildnauer et al. | 514/559 |

*Primary Examiner*—Zohreh Fay
*Attorney, Agent, or Firm*—Ivor M. Hughes; Neil H. Hughes; Marcelo K. Sarkis

[57] ABSTRACT

A preparation which is compatible with the skin for the treatment of labial disease and acne. The preparation comprises a mixture of:
- (a) at least one compound selected from an antiseptic compound and an anesthetic compound which is:
  - (i) a terpene,
  - (ii) a phenolic compound, or
  - (iii) an alcohol;
- (b) a quaternary ammonium antiseptic compound;
- (c) an antiseptic compound selected from compounds containing iodine, salts thereof and complexes thereof dissolved in an organic skin penetrating solvent, wherein said solvent comprises acetone.

41 Claims, No Drawings

TOPICAL TREATMENT OF DISEASED SKIN DISORDERS

This application is a continuation of U.S. application Ser. No. 08/108,167, filed Aug. 18, 1993, now abandoned, which is a continuation application of U.S. application Ser. No. 07/715,710, filed Jun. 18, 1991, now abandoned, which is a continuation application of U.S. application Ser. No. 07/476, 141, filed Feb. 7, 1990, now abandoned, which is a continuation application of U.S. application Ser. No. 07/242, 121, filed Sep. 9, 1988, now abandoned.

FIELD OF INVENTION

The present invention relates to a preparation of medicinal agents having a synergistic effect which has medical value in the topical treatment of a variety of diseased skin disorders including Herpes Simplex, acne, psoriasis, and dermatitis.

BACKGROUND OF THE INVENTION

Herpes Simplex infections described as Herpes labialis and Herpes nasalis are commonly known as cold sores and fever blisters. They cause painful itching and burning and great discomfort to those inflicted by them. Herpes genitalis is manifested by cycles of emerging skin lesions and eruptions which are also discomforting and lead to considerable levels of anxiety. As a venereal disease it has become more prevalent than syphilis or gonorrhea. Although many creams and ointments have been available over the years as medications, few have shown any significant levels of effectiveness. Acne vulgaris is a common disease, particularly among adolescents, which has as the characteristic lesions the open comedo (blackhead) and closed comedo. Although many have only mild acne some experience severe forms of acne and may lead to extensive scarring. Even the milder forms can cause considerable psychological distress for the individual. Psoriasis is a chronic disease characterized by epidermal hyperplasia and a greatly accelerated rate of epidermal production. The lesions are characteristically red, slightly raised and scaly. Instead of the normal 28 days from cell division in the basal layers until the cell is shed from the stratum corneum, in psoriasis it takes only 3 to 4 days for this to occur. The mechanism for this and the other signs and symptoms of psoriasis are not presently understood. Atopic dermatitis (eczema) is an allergic skin disease which is characterized by circumscribed discrete wheals with erythematous raised serpiginous borders and blanched centres and itching. Both children and adults are affected by this disease which is chronic and is further characterized by spontaneous exacerbations and remissions. It may last for years but does not last forever.

There have been and still are numerous products available to treat the symptoms of Herpes Simplex and acne. Many of these have incorporated an antiviral agent into ointments, creams, and lotions (U.K. patent 2 167 296 A, May 24, 1984). These have provided only limited degrees of relief in most cases and usually require frequent and continuous application. Many over-the-counter products contain ingredients which supposedly provide symptomatic relief of discomfort due to various skin conditions but none of which are claimed to be effective against Herpes infections except the recent drug, Acyclovir, which is claimed to have some topical activity. Consequently, Herpes victims usually have to suffer through the complete cycle of eruptions often leaving unpleasant skin blemishes. In addition to the lack of effectiveness of most products against lesions of Herpes infections, many do not satisfactorily alleviate the discomforts of the disease even during treatment and the products themselves are often messy and unpleasant to apply. Likewise, there have been very few treatments for psoriasis over the years but positive responses to treatment have been rarely found. Commonly, stiff, occlusive preparations which increase the hydration of dry, scaly skin have been used. These are often painful to apply and the preparation is messy usually leaving the patient discouraged. Also, current treatments of atopic dermatitis (eczema) have provided little beneficial effects or the drugs used (corticosteroids) have a high incidence of adverse side-effects. Treatment has often relied upon the properties of the pharmaceutical base to alter the extent of hydration of the skin.

Applicant is aware of a preparation sold under the trade mark "Blistex" used to treat cold sores. Applicant believes this product is petrolatum based. Applicant is also aware of a product bearing the trade mark "Listerine" used as a mouth wash and which Applicant believes comprises eucalyptol, menthol and thymol.

As a result of conducting a patent search, Applicant has become aware of (a) U.S. Pat. Nos. 4,262,007 and 4,390,539 which relate to a method for treating viral skin diseases including the use of benzethonium chloride;

(b) U.S. Pat. No. 4,130,638 which relates to a mouth wash containing alcohol and a flavouring agent selected from the group consisting of menthol, thymol, eucalyptol and anethol or mixtures thereof with peppermint oil;

(c) U.S. Pat. No. 3,408,298 which relates to a detergent germicidal composition comprising alkyl dimethyl benzyl ammonium chloride;

(d) U.S. Pat. No. 4,574,081 relating to an antiplaque dentifrice comprising an antiplaque quaternary ammonium compound, a flavouring agent comprising anethol and menthol;

(e) Canadian Letters Patent 899235 relating to a skin disinfectant composition comprising an aqueous solution of a complex of iodine with a mixture of alkyl dimethyl dichlorobenzyl ammonium chlorides in which the alkyl substituents contain 12 and 18 carbon atoms;

(f) U.S. Pat. No. 4,678,598 relating to a liquid shampoo comprising at least one surface active agent and a skin sensation inducing aromatic chemical selected from a group comprising among other chemicals menthol and cineol (which Applicant believes is another name for eucalyptol);

(g) Canadian Letters Patent 739927 relating to a thixotopic composition for treating skin maladies comprising alcohol and menthol;

(h) U.S. Pat. No. 4,702,916 relating to an analgesic stick comprising menthol;

(i) U.S. Pat. No. 4,669,491 at column 11, lines 39–46 relating to a biocide comprising at least one of 5-methyl-2-isopropyl-cyclohexanol, cineole and thymol amongst other chemicals;

(j) European Patent Application 86200131.0 relating to a method of killing viruses like Herpes virus Type I and Type II by contacting them with a viricidal composition comprising benzethonium chloride, ethanol, water, and a flavouring agent; and, (k) Romanian Reference 77453 relating to a medicament containing iodine.

According to the present invention there are provided novel compositions of matter for the treatment of dermal disease including labial, nasal, and genital lesions caused by Herpes Simplex, acne, psoriasis, and dermatitis. The novel pharmaceutical compositions comprise a combination of common medicinal agents, believed to act synergistically, one with the other, which exert a healing and a pain-relieving action. A solvent of acetone and water is preferred, believed to play a role in the effectiveness of the preparation but it is not considered essential to the overall synergistic action of the present invention.

The treatment of the skin diseases known as cold sores, fever blisters, genital herpes, psoriasis, acne, or eczema and the like using embodiments of the invention may be explained in part (in addition to the synergistic effect of combining the components) based on a completely different rationale than that which is currently practised. The inventor offers this explanation which should not be considered determinative of the operation of the formulations. It is offered solely to give the reader some insight of the inventors' consideration. Current modes of treatment are generally based on the application of medicament in a cream or ointment base having the properties of softening and lubricating the skin in the affected areas or promoting increased hydration of the stratum corneum layer of the epidermis. Although this often has the benefit of short-term relief of the discomfort and pain or itching from the diseased skin condition, this principle of treatment does not usually facilitate penetration of the medicament(s) into the skin or promote pharmacological action. In contrast, it is believed that application of the embodiments of the present invention immediately modify the dried keratin layer of the epidermis to enable rapid penetration of the antiseptic, anesthetic, and antipruritic agents as the case may be into the skin for relief of pain, itching, and the destruction of viral and bacterial cells which are the source of the diseased skin condition. In the case of psoriasis or certain types of eczema, embodiments of the present invention cause rapid sloughing off of the excess stratum corneum characteristic of these diseases, without the discomfort of inunction or the unpleasantness of a greasy layer on the skin. Consequently, the rapid return to a normal, healthy skin condition is obtained. It is because of this new approach to the treatment of these skin diseases that it is believed that the successes with volunteer subjects described in the examples have been obtained.

Formulations according to the present invention may also be formulated with other substances, for example, excipients, and may be in one of several galenical forms including a gel, a cream, a lotion, an ointment, or a paste, at various concentrations as necessary to exert the optimum effectiveness.

It is also believed that the present invention is effective in the manner described by combining at least three of the stated ingredients in a solution, for example of acetone and water or other aqueous solvent system.

Application of formulations according to the present invention to Herpes labialis (cold sores) in some cases stopped the cycle at one eruption, caused progression to the scab stage almost immediately, and the complete cycle was reduced to only a few days. Application to Herpes genitalis at the earliest stage in some cases resulted in only one eruption, the scab stage was begun immediately, and the cycle time was drastically reduced. Application to acne lesions in some cases caused them to vanish within hours and those in the prodromal stage aborted within 24 hours. Application to psoriasis in some cases removed the accumulation of corneal epidermis, alleviated pain, promoted healing, and its continued use eliminated any further accumulation of epidermal layers. One application of the present invention to atopic dermatitis (eczema) resulted in successful treatment whereas other modalities of treatment were less effective.

According to one aspect of the invention a preparation is provided which is compatible with the skin for the treatment of dermatologic diseases, for example labial, nasal and genital lesions caused by Herpes Simplex, acne, psoriasis and dermatitis the preparation comprising a mixture of (a) at least one antiseptic and/or anesthetic compound which is
  (i) a terpene (e.g. menthol and eucalyptol);
  (ii) a phenolic compound (e.g. thymol); or,
  (iii) an alcohol;
(b) a quaternary ammonium antiseptic compound;
(c) an antiseptic compound containing iodine, salts thereof and/or complexes thereof dissolved in an organic skin penetrating solvent.

According to another aspect of the invention, a method of treating dermatologic diseases (for example labial, nasal and genital lesions caused by Herpes Simplex, acne, psoriasis and dermatitis) is provided comprising administering an effective amount of a preparation compatible with the skin comprising a mixture of (a) at least one antiseptic and/or anesthetic compound which is
  (i) a terpene (e.g. menthol and eucalyptol);
  (ii) a phenolic compound (e.g. thymol); or,
  (iii) an alcohol;
(b) a quaternary ammonium antiseptic compound;
(c) an antiseptic compound containing iodine, salts thereof and/or complexes thereof dissolved in an organic skin penetrating solvent.

In one embodiment the selected antiseptic and/or anesthetic compound is a terpene and preferably the terpene is an oxygenated terpene. In another embodiment the quaternary ammonium antiseptic compound is benzethonium chloride. In another embodiment the antiseptic and/or anesthetic compound is a phenolic compound and the phenolic compound is thymol. In another embodiment the oxygenated terpene is selected from eucalyptol and menthol (which may also be considered an alcohol). In still another embodiment the oxygenated terpene comprises a mixture of eucalyptol and menthol. In still another embodiment the at least one antiseptic and/or anesthetic compound comprises a mixture of at least one phenolic compound and at least one terpene. Preferably the organic skin penetrating solvent is a mixture of acetone and water. In one embodiment at least one phenolic compound or at least one terpene comprises a mixture of eucalyptol, menthol and thymol. In this embodiment the quaternary ammonium antiseptic compound may be benzethonium chloride, the antiseptic compound containing iodine, salts thereof or complexes thereof comprises iodine and potassium iodide and the organic skin penetrating solvent is a mixture of acetone and water.

One embodiment of the present invention may comprise a solution of menthol, thymol, eucalyptol, potassium iodide, iodine, and benzethonium chloride in acetone:water or other aqueous solvent system. This, and other combinations of medicinal agents referred to above, all of which are presently commercially available, are effective treatments of the dermatologic skin disorders commonly referred to as cold sores, fever blisters, genital Herpes, psoriasis, eczema, and acne. The mechanisms of these actions are unknown but a response to treatment using the combinations has been observed to be markedly different than any of the individual component agents comprising the present invention. For instance, the antibacterial and bactericidal effects of potassium iodide, iodine, and benzethonium chloride are well known and they occur in many commercial products. However, combinations of these agents have not previously been employed in the particular manner described herein to treat the diseased skin disorders previously cited. Surprisingly, there are few topical skin treatments presently available, other than the present invention, which satisfactorily alleviate the pain, itching, and sensitivity of the skin to occurrences of the lesions of Herpes, the eruptions of acne, the dry, scaly condition of psoriasis, or the apparent rashed condition of eczema.

Typical amounts of the various components may include the following:

(a) the at least one antiseptic and/or anesthetic compound may be in a range of about 0.02%—about 2% by weight of the preparation;

(b) the quaternary ammonium antiseptic compound may be in the range of about 0.05%—about 3% by weight of the preparation;

(c) the antiseptic compound containing iodine, salts thereof and/or complexes thereof may be in the range of about 0.02%—about 2% by weight of the preparation.

The organic skin penetrating solvent may be in the range exceeding about 50%. The at least one antiseptic and/or anesthetic compound may comprise eugenol, camphor, hexetidine or anethol or the like. The organic skin penetrating solvent may comprise Dimethyl Sulfoxide (DMSO), azone, propylene glycol, dimethyl formamide, dimethyl acetamide, ethyl or isopropyl alcohol or the like in water. The quaternary ammonium antiseptic compound may be benzalkonium chloride, cetyl trimethylammonium bromide (CTAB) and cetyl pyridium chloride or the like.

As illustrated in the following examples, it is believed that the combination of ingredients act synergistically to produce the beneficial treatments observed.

EXAMPLE 1

A typical recipe of the synergistic combination of medicinal agents is as follows:

| | |
|---|---|
| Menthol | 1.25 g |
| Thymol | 0.25 g |
| Eucalyptol | 0.03 g |
| Potassium iodide | 0.03 g |
| Iodine | 0.03 g |
| Benzethonium chloride | 0.20 g |
| Acetone:water(70:30) qs | 60 ml |

The effectiveness of the present invention has been tested on volunteer patients. A full-scale clinical study has not yet been undertaken.

Directions (Treatment for Herpes Simplex I and II)

1. Apply liberally to the afflicted area 3 to 4 times over a one minute time period. Repeat every 3 minutes over a 10 minute period.
2. Repeat above procedure after approximately ½ to 1 hour.
3. To ensure virus activity is stopped repeat application as prescribed in initial treatment every 2 to 3 hours or until activity is stopped and healing is evident.
4. To hasten healing apply 2 to 3 applications twice daily. NOTE: If applied at the early prodromal stage (when a tingling sensation is first noticed) no blistering is evident.

For prodromal stage treatments use as prescribed in 1, 2 and 3.

EXAMPLE 2

Treatment of Herpes Simplex I (Herpes labialis)

No. of patients: approx. 12

The recipe according to Example 1 was prepared by dissolving and mixing the ingredients in a vehicle of acetone:water. Each patient was directed to apply the liquid directly to the cold sore using a cotton swab or other type of applicator. Optimum results were obtained when the preparation was applied liberally on the blistered area, the application repeated three times over a 10 min period, then repeated for three consecutive hours. Excellent results were also obtained when the treatment was applied twice a day for one day. The patients reported a very positive response to this treatment indicating an awareness of its immediate healing action. The cold sore quickly progressed to the scab stage and the lesion disappeared. No further eruptions occurred.

Each patient claimed that no other product was nearly as effective.

EXAMPLE 3

Treatment of Herpes Simplex II (Herpes genitalis)

No. of patients: 7

Each patient was directed to apply the liquid according to Example 1 to the eruptions in the same manner as described in Example 2. Again, the results were immediate. When applied at full cycle, drying of the eruptions occurred quickly and then progressed to the scab stage. If applied at the prodromal stage, so blistering was evident or only one eruption appeared and the cycle appeared stopped. Again, the patients reported that this treatment was far superior to any other products known to them. No side effects to this treatment were reported. Furthermore, earlier treatment diminished or eliminated the skin blemishes which are characteristic of the usual Herpes outbreak.

EXAMPLE 4

Treatment of Acne

No. of patients: 12

Each patient was directed to apply the liquid of Example 1 to open or closed comedos for 1 min, to repeat the application three times over a 10 min period, and to repeat the treatment after 2 hr. The results of the applications were pain relief immediately and reduction in size of the eruptions followed by complete disappearance within 2 to 3 days. When the medication was used in the prodromal stage, the comedos were abortive.

EXAMPLE 5

Treatment of Psoriasis

No. of patients: 3 (1 female, 2 males)

Each patient applied the liquid of Example 1 to red, dry, scaly epidermal skin for 2 min in the morning and again in the evening.

Directions (Treatment for Psoriasis)

1. Apply liberally to the afflicted area 3 to 4 times over a one minute time period. Repeat every 3 minutes over a 10 minute period.
2. The procedure is preferably carried out in the mornings.
3. This procedure is repeated after approximately ½ to 1 hour before going to bed.

A female patient proceeded with normal daily activities with her legs covered by nylon stockings. At the end of the day considerable sloughing of the corneal layer had occurred and this was easily washed off. A second application on the following day under the same conditions produced similar results but at this point the excess dead epidermal cells had essentially been removed and the skin was smooth and supple like normal skin. No particular discomfort or sensitivity was experienced during or following this treatment. Repeated treatments from time to time ensured that the symptoms of psoriasis did not reoccur. Patients reported this treatment to be far superior to any previous treatment practised with over-the-counter products or under the care of a physician.

It should be noted that over-use of this preparation after the build-up of skin has been eliminated may cause a drying effect. To eliminate drying and cracking of the tender pink skin the frequency of application of the preparation should be reduced and a skin moisturizing lotion (baby oil) applied.

EXAMPLE 6
Treatment of Atopic Dermatitis (Eczema)
No. of patients: 2

Generally, treatments of eczema using presently available commercial products serve to alleviate the symptoms of itching, soreness, and sensitivity to varying degrees. However, using the liquid preparation of Example 1 applied liberally on the infected area for 1 min, then repeated in 10 min caused the discrete wheals characteristic of this disease to soon disappear and the skin to return to its normal colour and texture. The patients reported that this treatment was more effective than any previous treatment attempted.

It is apparent that the beneficial therapeutic effects experienced by this limited number of volunteer patients are due to a synergistic action of the particular combination of medicinal agents described in the present invention. Although the present invention as described in Example 1 was accepted in that form by the patients, it is further apparent that for some applications certain types of galenical forms could increase the acceptance of this treatment of sensitive, visible parts of the anatomy.

As many changes can be made to the embodiment without departing from the scope of the invention, it is intended that all material contained herein be interpreted as illustrative of the invention and not in a limiting sense.

The embodiments of the invention in which an exclusive property or privilege is claimed are as follow:

1. A preparation which is compatible with the skin for the treatment of labial disease and acne, the preparation comprising a mixture of:
   (a) at least one compound selected from an antiseptic compound and an anesthetic compound which is:
      (i) a terpene,
      (ii) a phenolic compound, or
      (iii) an alcohol;
   (b) a quaternary ammonium antiseptic compound;
   (c) an antiseptic compound selected from compounds containing iodine, salts thereof and complexes thereof dissolved in an organic skin penetrating solvent, wherein said solvent comprises acetone.

2. The preparation of claim 1 wherein the terpene is an oxygenated terpene.

3. The preparation of claim 1 or 2 wherein the quaternary ammonium antiseptic compound is benzethonium chloride.

4. The preparation of claim 1 wherein the antiseptic an/or anesthetic compound is a phenolic compound and the phenolic compound is thymol.

5. The preparation of claim 2 wherein the oxygenated terpene is selected from eucalyptol and methol and mixtures thereof.

6. The preparation of claim 1 wherein the at least one compound selected from an antiseptic compound and an anesthetic compound comprises a mixture of at least one phenolic compound and at least one terpene.

7. The preparation of claim 6 wherein the at least one phenolic compound and at least one terpene comprises eucalyptol, menthol and thymol.

8. The preparation of claim 7 wherein the quaternary ammonium antiseptic compound is benzethonium chloride.

9. The preparation of claim 8 wherein the antiseptic compound containing iodine, its salts or complexes comprises iodine and potassium iodid.

10. The preparation of claim 9 wherein the organic skin penetrating solvent further comprises water.

11. A preparation for the treatment of the labia and acne comprising a mixture of menthol, thymol, eucalyptol, potassium iodide, iodine, and benzethonium chloride in a solution of acetone and water.

12. A preparation according to claim 11 formulated as a galenical form, selected from a gel, cream, lotion, ointment, or paste.

13. A method of treating labial diseases and acne comprising administering a preparation compatible with the skin for the treatment of labial diseases and acne, the preparation comprising a mixture of:
   (a) at least one compound selected from an antiseptic compound and an anesthetic compound which is;
      (i) a terpene,
      (ii) a phenolic compound, or
      (iii) an alcohol;
   (b) a quaternary ammonium antiseptic compound;
   (c) an antiseptic compound selected from compounds containing iodine, salts thereof and complexes thereof dissolved in an organic skin penetrating solvent, wherein said solvent comprises acetone.

14. The method of claim 13 wherein the terpene is an oxygenated terpene.

15. The method of claim 13 or 14 wherein the quaternary ammonium antiseptic compound is benzethonium chloride.

16. The method of claim 13 wherein the compound selected from an antiseptic compound and an anesthetic compound is a phenolic compound and the phenolic compound is thymol.

17. The method of claim 14 wherein the oxygenated terpene is selected from eucalyptol and methol and mixtures thereof.

18. The method of claim 13 wherein the at least one compound selected from an antiseptic compound and an anesthetic compound comprises a mixture of at least one phenolic compound and at least one terpene.

19. The method of claim 18 wherein the at least one phenolic compound and at least one terpene comprises eucalyptol, menthol and thymol.

20. The method of claim 19 wherein the quaternary ammonium antiseptic compound is benzethonium chloride.

21. The method of claim 20 wherein the antiseptic compound containing iodine, its salts or complexes comprises iodine and potassium iodide.

22. The method of claim 21 wherein the organic skin penetrating solvent further comprises water.

23. The preparation of claim 1 wherein the at least one compound selected from an antiseptic compound and an anesthetic compound comprises eugenol, camphor, hexetidine or anethol.

24. The preparation of claim 1 wherein the organic skin penetrating solvent may comprise dimethyl sulfoxide (DMS), azone, propylene glycol, dimethyl formamide, dimethyl acetamide, ethyl alcohol, isopropyl alcohol or the like in water.

25. The preparation of claim 1 wherein the quaternary ammonium antiseptic compound comprises a benzalkonium chloride, cetyl trimethylammonium bromide (CTAB) and cetyl pyridium chloride or the like.

26. The method of claim 13 wherein the at least one compound selected from an antiseptic compound and an anesthetic compound comprises eugenol, camphor, hexetidine or anethol or the like.

27. The method of claim 13 wherein the organic skin penetrating solvent may comprise dimethyl sulfoxide (DMSO), azone, propylene glycol, dimethyl formamide, dimethyl acetamide, ethyl alcohol, isopropyl alcohol or the like in water.

28. The method of claim 13 wherein the quaternary ammonium antiseptic compound may be a benzolkonium chloride, cetyl trimethylammonium bromide (CTGAB) and cetyl pyridium chloride or the like.

29. The preparation of claim 1 or 2 wherein
    (a) the at least one compound selected from an antiseptic compound and an anesthetic compound is in a range of about 0.02%—about 2% by weight of the preparation;
    (b) the quaternary ammonium antiseptic compound is in the range of about 0.05%—about 3% by weight of the preparation;
    (c) the antiseptic compound containing iodine, salts thereof and complexes are in the range of about 0.02%—about 2% by weight in preparation.

30. The preparation of claim 1 or 2 wherein the organic skin penetrating solvent may be in the range exceeding about 50%.

31. The preparation of claim 4, 5, or 6 wherein
    (a) the at least one compound selected from an antiseptic compound and an anesthetic compound is in a range of about 0.02%—about 2% by weight of the preparation;
    (b) the quaternary ammonium antiseptic compound is in the range of about 0.05%—about 3% by weight of the preparation;
    (c) the antiseptic compound containing iodine, salts thereof and complexes are in the range of about 0.02%—about 2% by weight in preparation.

32. The preparation of claim 8, 9, or 10 wherein
    (a) the at least one compound selected from an antiseptic compound and an anesthetic compound is in a range of about 0.02%—about 2% by weight of the preparation;
    (b) the quaternary ammonium antiseptic compound is in the range of about 0.05%—about 3% by weight of the preparation;
    (c) the antiseptic compound containing iodine, salts thereof and complexes are in the range of about 0.02%—about 2% by weight in preparation.

33. The preparation of claim 10, 24, or 27 wherein the organic skin penetrating solvent exceeds about 50%.

34. The method of claim 13 or 14 wherein
    (a) the at least one compound selected from an antiseptic compound and an anesthetic compound is in a range of about 0.02%—about 2% by weight of the preparation;
    (b) the quaternary ammonium antiseptic compound is in the range of about 0.05%—about 3% by weight of the preparation;
    (c) the antiseptic compound containing iodine, salts thereof and complexes are in the range of about 0.02%—about 2% by weight in preparation.

35. The method of claim 14, 15, or 16 wherein (a) the at least one compound selected from an antiseptic compound and an anesthetic compound is in a range of about 0.02%—about 2% by weight of the preparation;

(b) the quaternary ammonium antiseptic compound is in the range of about 0.05%—about 3% by weight of the preparation;

(c) the antiseptic compound containing iodine, salts thereof and complexes are in the range of about 0.02%—about 2% by weight in preparation.

36. The method of claim 17, 18, or 19 wherein
    (a) the at least one compound selected from an antiseptic compound and an anesthetic compound is in a range of about 0.02%—about 2% by weight of the preparation;
    (b) the quaternary ammonium antiseptic compound is in the range of about 0.05%—about 3% by weight of the preparation;
    (c) the antiseptic compound containing iodine, salts thereof and complexes are in the range of about 0.02%—about 2% by weight in preparation.

37. The method of claim 20, 21, or 25 wherein
    (a) the at least one compound selected from an antiseptic compound and an anesthetic compound is in a range of about 0.02%—about 2% by weight of the preparation;
    (b) the quaternary ammonium antiseptic compound is in the range of about 0.05%—about 3% by weight of the preparation;
    (c) the antiseptic compound containing iodine, salts thereof and complexes are in the range of about 0.02%—about 2% by weight in preparation.

38. The method of claim 27 wherein
    (a) the at least one compound selected from an antiseptic compound and an anesthetic compound is in a range of about 0.02%—about 2% by weight of the preparation;
    (b) the quaternary ammonium antiseptic compound is in the range of about 0.05%—about 3% by weight of the preparation;
    (c) the antiseptic compound containing iodine, salts thereof and complexes are in the range of about 0.02%—about 2% by weight in preparation.

39. The method of claim 26 wherein the organic skin penetrating solvent may be in the range exceeding about 50%.

40. The preparation of claim 11 or 12 wherein said mixture comprises:
    about 1.67% by weight of Menthol,
    about 0.34% by weight of Thymol,
    about 0.04% by weight of Eucalyptol,
    about 0.04% by weight of Iodine,
    about 0.04% by weight of Potassium Iodid,
    about 0.66% by volume of Benzethronium Chloride,
    about 65% by volume of Acetone, and
    about 23.4% by volume of Water.

41. The preparation of claims 9 or 12 wherein said mixture comprises:
    about 0.9% by weight of Menthol,
    about 0.34% by weight of Thymol,
    about 0.13% by weight of Benzethonium Cl,
    about 0.12% by weight of K Iodide,
    about 0.12% by weight of Iodine,
    about 0.04% by weight of Eucalyptus Oil
    about 8.0% by weight of Glycerine,
    about 0.75% by weight of Natrosol,
    about 0.04% by weight of Lavender Oil,
    about 44% by volume of Water,
    about 45% by volume of Acetone.

\* \* \* \* \*